(12) United States Patent
Schmitt et al.

(10) Patent No.: US 7,579,301 B2
(45) Date of Patent: Aug. 25, 2009

(54) HERBICIDAL COMPOSITIONS COMPRISING BENZOYLPYRAZOLES AND SAFENERS

(75) Inventors: Monika H. Schmitt, Frankfurt am Main (DE); Lothar Willms, Hofheim (DE); Frank Ziemer, Kriftel (DE); Christopher Rosinger, Hofheim (DE); Hermann Bieringer, Eppstein (DE); Philipp Huff, Eppstein-Vockenhausen (DE); Erwin Hacker, Hochheim (DE)

(73) Assignee: Bayer CropScience AG, Frankfurt am Main (DE)

( * ) Notice: Subject to any disclaimer, the term of this patent is extended or adjusted under 35 U.S.C. 154(b) by 469 days.

(21) Appl. No.: 11/069,222

(22) Filed: Feb. 28, 2005

(65) Prior Publication Data

US 2005/0148471 A1    Jul. 7, 2005

Related U.S. Application Data

(62) Division of application No. 10/300,353, filed on Nov. 20, 2002, now Pat. No. 6,872,691.

(51) Int. Cl.
*A01N 25/00* (2006.01)
*A01N 25/32* (2006.01)

(52) U.S. Cl. .................. 504/116.1; 504/103
(58) Field of Classification Search ........... None
See application file for complete search history.

(56) References Cited

U.S. PATENT DOCUMENTS

| 5,824,802 | A | 10/1998 | Benko et al. |
| 6,420,317 | B1 * | 7/2002 | Schmitt et al. ............. 504/282 |
| 6,448,201 | B1 | 9/2002 | Seitz et al. |
| 6,511,940 | B1 | 1/2003 | Ziemer et al. |
| 6,569,805 | B1 * | 5/2003 | Krahmer et al. ............. 504/103 |
| 6,603,044 | B1 | 8/2003 | Tohnishi et al. |
| 6,660,691 | B2 | 12/2003 | Ziemer et al. |
| 6,872,691 | B2 * | 3/2005 | Schmitt et al. ............. 504/282 |
| 2004/0087445 | A1 | 5/2004 | Ziermer et al. |

FOREIGN PATENT DOCUMENTS

| AU | 2001/3701 | | 2/2002 |
| AU | 2000/7302 | | 3/2002 |
| DE | 199 61 465 | A1 | 7/2000 |
| DE | 10159659 | A1 | 6/2003 |
| EP | 00203428 | A1 | 12/1986 |
| WO | WO 99/58509 | | 11/1999 |
| WO | WO-99/66795 | | 12/1999 |
| WO | WO 00/30447 | | 6/2000 |
| WO | WO 01/74785 | A1 | 10/2001 |
| WO | WO-02/098229 | A1 | 12/2002 |
| WO | WO-03/043423 | A1 | 5/2003 |

OTHER PUBLICATIONS

English language abstract of DE 199 61 465.

* cited by examiner

*Primary Examiner*—Johann R Richter
*Assistant Examiner*—Kristie L Brooks
(74) *Attorney, Agent, or Firm*—Connolly Bove Lodge & Hutz LLP

(57) ABSTRACT

What is described are herbicidal compositions comprising herbicidal compounds of the formula I

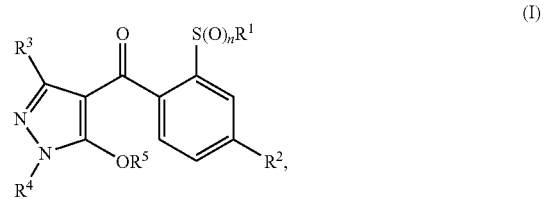

(I)

and a compound which acts as safener. In the formula I, the symbols $R^1$ to $R^4$ denote hydrogen, halogen, alkyl and haloalkyl.

10 Claims, No Drawings

HERBICIDAL COMPOSITIONS COMPRISING BENZOYLPYRAZOLES AND SAFENERS

The invention relates to the technical field of the crop protection products, in particular herbicide/antidote combinations (active ingredient/safener combinations) which are suitable for use against competing harmful plants in crops of useful plants.

A large number of herbicidal active ingredients are known as inhibitors of the enzyme p-hydroxyphenylpyruvate dioxygenase (HPPD). Only recently, more such active ingredients were disclosed, for example in WO 99/58509 and DE 10016116.2.

As is the case with many other herbicidal active ingredients, these HPPD inhibitors are also not always sufficiently well tolerated by (i.e. not sufficiently selective in) some important crop plants such as corn, rice or cereals, so that their use is very limited. They can therefore not be employed in some crops, or only at such low application rates that the desired broad herbicidal activity against harmful plants is not ensured. Specifically, many of the abovementioned herbicides cannot be employed as fully selective herbicides against harmful plants in corn, rice, cereals, sugar cane and some other crops.

To overcome these disadvantages, it is known to employ herbicidal active ingredients in combination with what is known as a safener or antidote. Thus, for example, WO 99/66795 and WO 00/30447 describes various combinations of a large number of HPPD inhibitors with a multiplicity of safeners. Inter alia, WO 00/30447 also describes benzoylpyrazoles in combination with different safeners.

A safener is understood as meaning a compound which compensates for, or reduces, the phytotoxic properties of a herbicide with regard to useful plants, without substantially reducing the herbicidal activity against harmful plants.

Finding a safener for a specific group of herbicides remains a difficult task since the mechanisms by which a safener reduces the harmful action of herbicides are not known in detail. The fact that a compound in combination with a specific herbicide acts as safener therefore allows no conclusions to be drawn as to whether such a compound also has a safener action with other groups of herbicides. Thus, it has emerged when safeners are used for protecting the useful plants from herbicide damage that the safeners may still exhibit certain disadvantages in many cases. These include:
- the safener reduces the activity of the herbicide against the harmful plants,
- the useful-plant protecting properties are insufficient,
- the spectrum of the useful plants in which the safener/herbicide is to be employed is not sufficiently wide in combination with a given herbicide,
- a given safener cannot be combined with a sufficiently large number of herbicides.

It was an object of the present invention to provide further combinations of herbicides from the group of the HPPD inhibitors with safeners which are suitable for increasing the selectivity of these herbicides with regard to important crop plants.

There have now been found novel combinations of specific herbicides from the group of the HPPD inhibitors, specifically from the group of the benzoylpyrazoles which have selected substituents attached in the 2 and 4-positions of the benzoyl moiety, with some selected safeners which increase the selectivity of these herbicides with regard to important crop plants.

The invention therefore relates to a herbicidally active composition comprising
A) a herbicidally effective amount of one or more compounds of the formula (I), if appropriate also in the form of their salts,

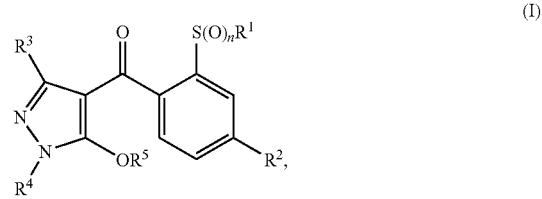

where
$R^1$ is methyl or ethyl;
$R^2$ is trifluoromethyl, fluorine, chlorine or bromine;
$R^3$ is hydrogen or methyl;
$R^4$ is methyl or ethyl;
$R^5$ is hydrogen, methylsulfonyl, ethylsulfonyl, n-propylsulfonyl, phenylsulfonyl, 4-methylphenylsulfonyl, benzyl, benzoylmethyl, nitrobenzoylmethyl or 4-fluorobenzoylmethyl and
n is 0, 1, or 2, and
B) an antidote-effective amount of at least one compound (component B) from one of the groups B1 to B6:
B1 compounds of the formula II

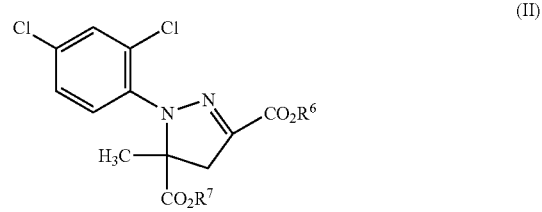

where $R^6$ and $R^7$ independently of one another are hydrogen or $(C_1-C_4)$-alkyl;
B2 compounds of the formula III

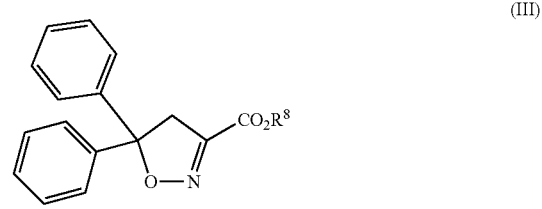

where $R^8$ is hydrogen or $(C_1-C_4)$-alkyl;
B3 oxabetrinil, fluxofenim, fenclorim, flurazole, cloquintocet-mexyl, dichlormid, benoxacor, furilazole, 4-dichloroacetyl-1-oxa-4-aza-spiro[4,5]decane (AD-67);
B4 1,8-naphthalic anhydride, methyl diphenylmethoxyacetate, cyanomethoxyimino(phenyl)acetonitrile (cyometrinil), 2-dichloromethyl-2-methyl-1,3-dioxolane (MG-191), N-(4-methylphenyl)-N'-(1-methyl-1-phenylethyl) urea (dymron), 1-[4-(N-2-methoxybenzoylsulfamoyl) phenyl]-3-methylurea, 1-[4-(N-2- methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea, 1-(ethoxycarbonyl)ethyl 3,6-dichloro-2-methoxybenzoate (lactidichlor) and their salts and esters, preferably ($C_1$-$C_8$), 3-dichloroacetyl-2,2,5-trimethyloxazolidine, 1,3-dimethylbut-1-yl (5-chloro-8-quinolineoxy)acetate, 4-allyloxybutyl (5-chloro-8-quinolineoxy)acetate, 1-allyloxyprop-2-yl (5-chloro-8-quinolineoxy)acetate, ethyl (5-chloro-8-quinolineoxy)acetate, methyl (5-chloro-8-quinolineoxy)acetate, allyl (5-chloro-8-quinolineoxy)acetate, 2-(2-propylideneiminooxy)-1-ethyl (5-chloro-8-quinolineoxy)acetate, 2-oxoprop-1-yl (5-chloro-8-quinolineoxy)acetate;

B5 acylsulfamoylbenzamides of the formula (IV), if appropriate also in salt form,

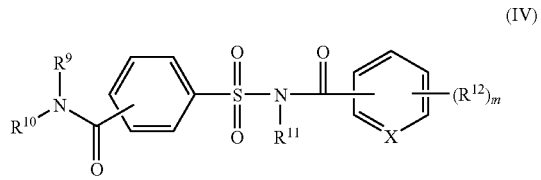

(IV)

where
x is CH or N;
$R^9$ is hydrogen, ($C_1$-$C_6$)-alkyl, ($C_3$-$C_6$)-cycloalkyl, ($C_2$-$C_6$)-alkenyl, ($C_2$-$C_6$)-alkynyl, where the four last mentioned radicals are unsubstituted or substituted by one or more identical or different substituents from the group consisting of halogen, ($C_1$-$C_6$)-alkoxy, ($C_1$-$C_6$)-haloalkoxy, ($C_1$-$C_2$)-alkylsulfinyl, ($C_1$-$C_2$)-alkylsulfonyl, ($C_3$-$C_6$)-cycloalkyl, ($C_1$-$C_4$)-alkoxycarbonyl, ($C_1$-$C_4$)-alkylcarbonyl and, in the case of cyclic radicals, also ($C_1$-$C_4$)-alkyl and ($C_1$-$C_4$)-haloalkyl;
$R^{10}$ is hydrogen, ($C_1$-$C_6$)-alkyl, ($C_2$-$C_6$)-alkenyl, ($C_2$-$C_6$)-alkynyl, where the three last mentioned radicals are unsubstituted or substituted by one or more identical or different substituents from the group consisting of halogen, ($C_1$-$C_4$)-alkyl, ($C_1$-$C_4$)-alkoxy and ($C_1$-$C_4$)-alkylthio, or
$R^9$ and $R^{10}$ together with the nitrogen atom carrying them form a pyrrolidinyl or piperidinyl radical;
$R^{11}$ is hydrogen, ($C_1$-$C_4$)-alkyl, ($C_2$-$C_4$)-alkenyl or ($C_1$-$C_4$)-alkynyl;
$R^{12}$ are identical or different and are halogen, nitro, ($C_1$-$C_4$)-alkyl, ($C_1$-$C_4$)-haloalkyl, ($C_1$-$C_4$)-haloalkoxy, ($C_1$-$C_4$)-alkoxy, cyano, ($C_1$-$C_4$)-alkylthio, ($C_1$-$C_4$)-alkylsulfinyl, ($C_1$-$C_4$)-alkylsulfonyl,
m is 0, 1 or 2;
B6 N-acylsulfonamides of the formula (V) and their salts

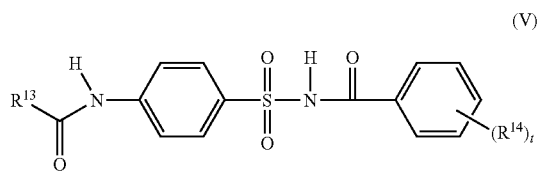

(V)

where
$R^{13}$ is hydrogen, ($C_1$-$C_6$)-alkyl, ($C_3$-$C_6$)-cycloalkyl, where each of the 2 last mentioned radicals is unsubstituted or substituted by one or more substituents from the group consisting of halogen, ($C_1$-$C_4$)-alkoxy, halo-($C_1$-$C_6$)-alkoxy and ($C_1$-$C_4$)-alkylthio and, in the case of cyclic radicals, also ($C_1$-$C_4$)-alkyl and ($C_1$-$C_4$)-haloalkyl,
$R^{14}$ is halogen, ($C_1$-$C_4$)-alkyl, ($C_1$-$C_4$)-haloalkyl, such as trifluoromethyl, halo-($C_1$-$C_4$)-alkoxy, ($C_1$-$C_4$)-alkoxy or ($C_1$-$C_4$)-alkylthio,
t is 1 or 2, including the stereoisomers and the agriculturally useful salts.

Herbicidally active amount for the purposes of the invention refers to an amount of one or more herbicides suitable for having an adverse effect on plant growth.

Antidote-effective amount for the purposes of the invention refers to an amount of one or more safeners suitable for at least partially counteracting the phytotoxic effect of a herbicide or herbicide mixture on a useful plant.

Unless specifically defined otherwise, the definitions given hereinbelow generally apply to the radicals in the formula (I).

Alkyl, also in the composite meanings such as alkoxy or haloalkoxy, denotes, for example, methyl, ethyl, n- or i-propyl, n-, i-, t- or 2-butyl, n-pentyl and n-hexyl. The meanings of alkenyl and alkynyl are to be understood analogously.

Formulae (I) to (V) also encompass all stereoisomers which have the same topological linkage of the atoms, and their mixtures. Such compounds contain one or more asymmetric carbon atoms and/or double bonds. The possible enantiomers and/or diastereomers, defined by their specific spatial form, can be obtained from stereoisomer mixtures by customary methods or else be prepared by stereoselective reactions in combination with the use of stereochemically pure starting materials.

Suitable herbicidally active compounds are, in accordance with the invention, those compounds of the formula (I) which cannot be employed on their own, or which cannot be employed optimally, in crops of useful plants such as cereal crops, rice or corn since they cause too much damage to the crop plants.

Herbicides of the formula (I) are known, for example, from DE 10016116.2. The compounds of group B1 are known from U.S. Pat. No. 5,703,008 and U.S. Pat. No. 5,700,758. The compounds of group B2 are known from WO 95/07897 and the literature cited therein. The chemical structures of the active compounds of group B3, referred to by their common names, are known, for example, from "The Pesticide Manual", 12th edition, 2000, British Crop Protection Council. The compounds of group B4 are known, for example, from EP-A-0 086 750, EP-A-0 94349 (U.S. Pat. No. 4,902,340), EP-A-0 191736 (U.S. Pat. No. 4,881,966) and EP-A-0 492 366 and the literature cited therein. The compounds of group B5 are described in WO-A-97/45016, those of group B6 in the German patent application 197 42 951.3. The publications cited above contain detailed information on preparation processes and starting materials. These publications are expressly referred to; by reference, they are incorporated into this description.

For the purposes of the present application, the terms "herbicidal compositions" and "herbicide/safener combinations" are to be considered as having the same meaning.

Preference is given to herbicidal compositions comprising one of the herbicidally active compounds of the formula (Ia) comprising the compounds A1, A2, A3 and A4:

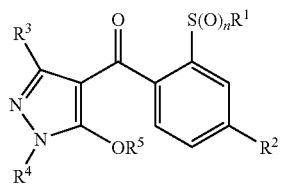

| No. | R¹ | R² | R³ | R⁴ | R⁵ | n |
|-----|-----|-----|-----|-----|-----|---|
| (A1) | CH₃ | CF₃ | H | CH₃ | H | 2 |
| (A2) | CH₃ | CF₃ | CH₃ | CH₃ | H | 2 |
| (A3) | CH₃ | CF₃ | CH₃ | CH₂CH₃ | H | 2 |
| (A4) | CH₃ | CF₃ | H | CH₂CH₃ | H | 2 |

Preference is also given to herbicidal compositions comprising, as safener, one or more compounds from the group comprising the compounds mefenpyr-diethyl (B1.1), oxabetrinil (B3.1), fluxofenim (B3.2), fenclorim (B3.3), flurazole (B3.4), cloquintocet-mexyl (B3.5), dichlormid (B3.6), benoxacor (B3.7), furilazole (B3.8) and the compounds B2.1, B2.2, B2.3, B5.1, B5.2, B5.3, B5.4, B5.5, B5.6 and B5.7:

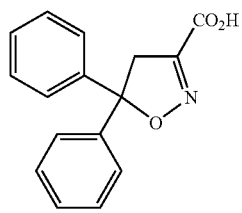
(B2.1)

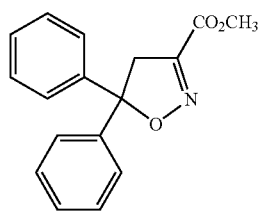
(B2.2)

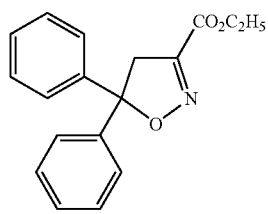
(B2.3)

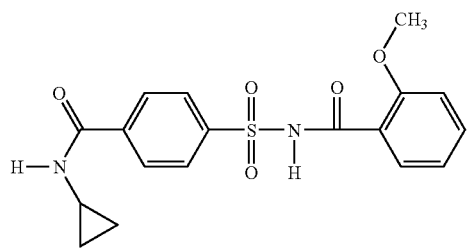
(B5.1)

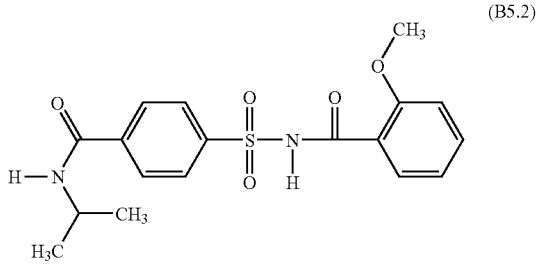
(B5.2)

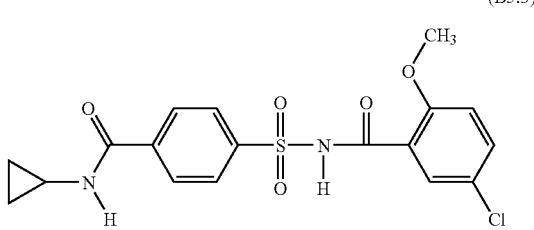
(B5.3)

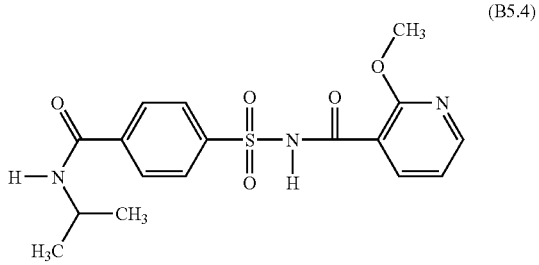
(B5.4)

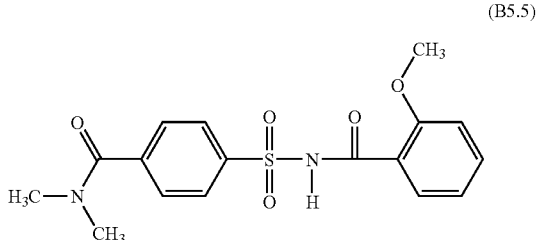
(B5.5)

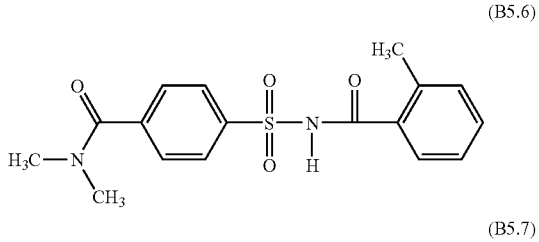
(B5.6)

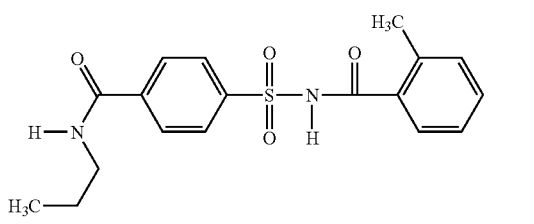
(B5.7)

Particular preference is given to herbicidal compositions comprising the following combinations of two compounds (A)+(B):

(A1)+(B1.1), (A1)+(B2.1), (A1)+(B2.2), (A1)+(B2.3), (A1)+(B3.1), (A1)+(B3.2), (A1)+(B3.3), (A1)+(B3.4), (A1)+(B3.5), (A1)+(B3.6), (A1)+(B3.7), (A1)+(B3.8), (A1)+(B5.1), (A1)+(B5.2), (A1)+(B5.3), (A1)+(B5.4), (A1)+(B5.5), (A1)+(B5.6), (A1)+(B5.7);
(A2)+(B1.1), (A2)+(B2.1), (A2)+(B2.2), (A2)+(B2.3), (A2)+(B3.1), (A2)+(B3.2), (A2)+(B3.3), (A2)+(B3.4), (A2)+(B3.5), (A2)+(B3.6), (A2)+(B3.7), (A2)+(B3.8), (A2)+(B5.1), (A2)+(B5.2), (A2)+(B5.3), (A2)+(B5.4), (A2)+(B5.5), (A2)+(B5.6), (A2)+(B5.7);
(A3)+(B1.1), (A3)+(B2.1), (A3)+(B2.2), (A3)+(B2.3), (A3)+(B3.1), (A3)+(B3.2), (A3)+(B3.3), (A3)+(B3.4), (A3)+(B3.5), (A3)+(B3.6), (A3)+(B3.7), (A3)+(B3.8), (A3)+(B5.1), (A3)+(B5.2), (A3)+(B5.3), (A3)+(B5.4), (A3)+(B5.5), (A3)+(B5.6), (A3)+(B5.7);
(A4)+(B1.1), (A4)+(B2.1), (A4)+(B2.2), (A4)+(B2.3), (A4)+(B3.1), (A4)+(B3.2), (A4)+(B3.3), (A4)+(B3.4), (A4)+(B3.5), (A4)+(B3.6), (A4)+(B3.7), (A4)+(B3.8), (A4)+(B5.1), (A4)+(B5.2), (A4)+(B5.3), (A4)+(B5.4), (A4)+(B5.5), (A4)+(B5.6), (A4)+(B5.7).

The compounds mentioned herein as safeners (antidotes) reduce or compensate for phytotoxic effects which may occur when using the herbicidally active compounds of the formula (I) in crops of useful plants without essentially adversely affecting the efficacy of these herbicidally active compounds against harmful plants. Thus, the field of application of conventional crop protection agents can be widened considerably and extended to, for example, crops such as wheat, barley, rice and corn in which the use of the herbicides has previously not been possible or only with limitations, that is to say at low dosages with a narrow spectrum of action.

The herbicidally active compounds and the safeners mentioned can be applied together (as ready mix or by the tank mix method) or sequentially in any desired sequence. The weight ratio of safener to herbicidally active compound may vary within wide limits and is preferably in the range of from 1:100 to 100:1, in particular from 1:10 to 10:1. The optimum amounts of herbicidally active compound and safener depend in each case on the type of the herbicidally active compound used or on the safener used and on the nature of the plant stock to be treated and can be determined in each individual case by simple routine preliminary experiments.

The combinations according to the invention are preferably used for controlling unwanted harmful plants in corn and cereal crops such as, for example, wheat, rye, barley, oats, rice, sorghum, but also cotton, sugar beet, sugar cane and soybean, preferably cereals, rice and corn.

Depending on their properties, the safeners employed in accordance with the invention may be used for pretreating the seed of the crop plant (seed dressing) or introduced into the seed furrows prior to sowing or used together with the herbicide before or after emergence of the plants. Pre-emergence treatment includes not only the treatment of the area under cultivation before sowing, but also the treatment of the sown soil which does not yet sustain vegetation. Preferred is the application together with the herbicide. Tank mixes or ready mixes may be employed for this purpose.

The safener application rates required may vary within wide limits, depending on the indication and the herbicidally active compound used; they are, as a rule, in the range of from 0.001 to 5 kg, preferably from 0.005 to 0.5 kg, of active compound per hectare.

The present invention therefore also relates to a method of protecting crop plants from phytotoxic side effects of herbicides of the formula (I), which comprises applying an antidote-effective amount of one or more compounds of component B before, after or simultaneously with the herbicidally active compound A of the formula (I) to the plants, plant seeds or the area under cultivation.

The herbicide/safener combination according to the invention may also be employed for controlling harmful plants in crops of known genetically modified plants or genetically modified plants yet to be developed. As a rule, the transgenic plants are distinguished by particularly advantageous properties, for example by resistances to certain crop protection agents, resistances to plant diseases or to causative agents of plant diseases such as specific insects or microorganisms such as fungi, bacteria or viruses. Other particular properties concern for example the harvested crop with regard to quantity, quality, storability, composition and specific constituents. Thus, transgenic plants are known with an increased starch content or a modified starch quality, or those with a different fatty acid composition of the harvested crop.

Preferred is the use of the combinations according to the invention in economically important crops of transgenic useful plants, for example of cereals such as wheat, barley, rye, oats, millet rice, cassava and corn, or else crops of sugar beet, sugar cane, cotton, soybean, oilseed rape, potato, tomato, pea and other vegetables.

When the combinations according to the invention are used in transgenic crops, effects in addition to the effects to be observed against harmful plants in other crops are frequently found, which are specific for application in the particular transgenic crop, for example a modified or specifically widened weed spectrum which can be controlled, modified application rates which may be employed for the application, preferably good combinability with the herbicides to which the transgenic crop is resistant, and an effect on growth and yield of the transgenic crop plants.

The invention thus also relates to the use of the combination according to the invention for controlling harmful plants in transgenic crop plants.

The safeners of component B and their combinations with one or more of the abovementioned herbicidally active compounds of the formula (I) can be formulated in various ways, depending on the prevailing biological and/or chemico-physical parameters. Suitable possibilities of formulation are, for example, wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed-dressing products, granules (GR) in the form of microgranules, spray granules, coated granules and absorption granules, granules for soil application or broadcasting, water-soluble granules (SG), water-dispersible granules (WG), ULV formulations, microcapsules and waxes.

These individual formulation types are known in principle and are described, for example, in: Winnacker-Kuchler, "Chemische Technologie" [Chemical engineering], Volume 7, C. Hauser Verlag Munich, 4th Ed., 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries which may be required, such as inert materials, surfactants, solvents and further additives are likewise known and described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co.

Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Based on these formulations, combinations with other crop protectants such as insecticides, acaricides, herbicides, fungicides, and with safeners, fertilizers and/or growth regulators may also be prepared, for example in the form of a readymix or a tank mix.

Wettable powders are preparations which are uniformly dispersible in water and which, besides the active compound, additionally comprise ionic and/or nonionic surfactants (wetters, dispersants), for example polyoxethylated alkylphenols, polyoxethylated fatty alcohols, polyoxethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate, or else sodium oleoylmethyltaurinate, in addition to a diluent or inert substance. To prepare the wettable powders, the herbicidally active compounds are ground finely, for example in customary apparatuses such as hammer mills, blower mills and air-jet mills, and simultaneously or subsequently mixed with the formulation auxiliaries.

Emulsifiable concentrates are prepared for example by dissolving the active compound in an organic solvent, for example butanol, cyclohexanone, DMF or else high-boiling hydrocarbons such as saturated or unsaturated aliphatic or alicyclic substances, aromatic substances or mixtures of these organic solvents with addition of one or more ionic and/or nonionic surfactants (emulsifiers). The following are examples of emulsifiers which may be used: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as polyoxyethylene sorbitan fatty acid esters. Dusts are obtained in general by grinding the active compound with finely divided solid materials, for example talc, natural clays such as kaolin, bentonite and pyrophyllite, or diatomaceous earth.

Suspension concentrates may be water- or oil-based. They can be prepared for example by wet-milling by means of commercially available bead mills, if appropriate with addition of surfactants as, for example, have already been listed above in the case of the other formulation types.

Emulsions, for example oil-in-water emulsions (EW), can be prepared for example by means of stirrers, colloid mills and/or static mixers using aqueous organic solvents and, if appropriate, surfactants as, for example, have already been listed above in the case of the other formulation types.

Granules can be produced either by spraying the active compound onto adsorptive granulated inert material or by applying active compound concentrates to the surface of carriers such as sand, kaolinite or of granulated inert material by means of binders, for example polyvinyl alcohol, sodium polyacrylate or else mineral oils. Suitable active compounds may also be granulated in the manner which is conventional for the production of fertilizer granules, if desired as a mixture with fertilizers.

As a rule, water-dispersible granules are prepared by the customary methods such as spray-drying, fluidized-bed granulation, disk granulation, mixing by means of high-speed mixers, and extrusion without solid inert material.

To prepare disk, fluidized-bed, extruder and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57.

For further details on the formulation of crop protection agents see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of active compounds from group B or of the herbicide/antidote active compound mixture (I) B and from 1 to 99.9% by weight, in particular from 5 to 99.8% by weight, of a solid or liquid additive and from 0 to 25% by weight, in particular from 0.1 to 25% by weight, of a surfactant.

In wettable powders, the active compound concentration is, for example, from approximately 10 to 90% by weight, the remainder to 100% by weight being composed of customary formulation components. In the case of emulsifiable concentrates, the concentration amounts to approximately 1 to 80% by weight. Formulations in the form of dusts comprise from approximately 1 to 20% by weight of active compounds, sprayable solutions from approximately 0.2 to 20% by weight of active compounds. In the case of granules such as water-dispersible granules, the active compound content depends partly on whether the active compound is in liquid or solid form. As a rule, the active compound content in the water-dispersible granules is between 10 and 90% by weight. In addition, the active compound formulations mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The necessary application rate of the herbicides of the formula (I) varies with the external conditions such as, inter alia, temperature, humidity and the type of the herbicide used. It can be varied within wide limits, for example between 0.001 and 10.0 kg/ha or more of active substance, but it is preferably between 0.005 and 5 kg/ha.

The examples which follow illustrate the invention:

A FORMULATION EXAMPLES a) A dust is obtained by mixing 10 parts by weight of a compound of group B or of an active compound mixture of a herbicidally active compound of the formula (I) and a compound of group B and 90 parts by weight of talc as inert substance and comminuting the mixture in a hammer mill.

b) A wettable powder which is readily dispersible in water is obtained by mixing 25 parts by weight of a compound of group B or of an active compound mixture of a herbicidally active compound of the formula (I) and a compound of group B, 64 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of group B or of an active compound mixture of a herbicidally active compound of the formula (I) and a compound of group B, 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a bowl mill to a fineness of below 5 microns.

d) An emulsifiable concentrate is obtained from 15 parts by weight of a compound of group B or of an active compound mixture of a herbicidally active compound of the formula (I) and a compound of group B, 75 parts by weight of cyclohexanone as solvent and 10 parts by weight of oxethylated nonylphenol as emulsifier.

e) Water-dispersible granules are obtained by mixing

| | |
|---|---|
| 75 parts by weight | of a compound of group B or of an active compound mixture of a herbicidally active compound of the formula (I) and a compound of group B, |
| 10 parts by weight | of calcium lignosulfonate, |
| 5 parts by weight | of sodium lauryl sulfate, |
| 3 parts by weight | of polyvinyl alcohol and |
| 7 parts by weight | of kaolin, | grinding the mixture on a pinned-disk mill and granulating the powder in a fluidized bed by spraying on water as granulation liquid.

f) Water-dispersable granules are also obtained by homogenizing and precomminuting

| | |
|---|---|
| 25 parts by weight | of a compound of group B or of an active compound mixture of a herbicidally active compound of the formula (I) and a compound of group B, |
| 5 parts by weight | of sodium 2,2'-dinaphthylmethane-6,6'-disulfonate, |
| 2 parts by weight | of sodium oleoylmethyltaurinate, |
| 1 parts by weight | of polyvinyl alcohol, |
| 17 parts by weight | of calcium carbonate and |
| 50 parts by weight | of water | in a colloid mill, subsequently milling the mixture in a bead mill and atomizing and drying the resulting suspension in a spray tower by means of a single-substance nozzle.

B BIOLOGICAL EXAMPLES

Post-Emergence Experiments:

Seeds of useful plants are placed in soil in the open and covered with soil. At the three-leaf stage, i.e. approximately three weeks after the start of cultivation, the plants are treated with the herbicides formulated as emulsifiable concentrates or dusts and safeners in the form of aqueous dispersions or suspensions or emulsions at an application rate of 300 to 800 l of water per ha (converted) at various dosages. The damage to the useful plants is scored visually 14 days after the treatment. The results demonstrate that the damage in the useful plants can be reduced considerably by using the compositions according to the invention comprising herbicide and safener in comparison with using the herbicide only. Depending on the rate of application, the species of the useful plant and the type of the composition according to the invention, the damage is reduced by up to 100% in comparison with using the herbicide only.

The test results of some herbicidal compositions according to the invention comprising herbicide and safener are shown in the tables below.

Table 2 shows the reduction of the damage to the crop plant wheat when using the compositions according to the invention, compared to the use of the herbicide on its own. Table 3 shows the reduction of the damage to different cultivars of the crop plant corn when using the compositions according to the invention, compared to the use of the herbicide on its own.

TABLE 1

Structure herbicide A2 safener B1.1 safener B5.1 safener B2.3

TABLE 2

| Compound | Dosage [g of a.i./ha] | Reduction of damage in wheat |
|---|---|---|
| A2 + B1.1 | 75 + 15 | −56% |

TABLE 3

| Compound | Dosage [g of a.i./ha] | Reduction of damage in corn |
|---|---|---|
| A2 + B5.1 | 200 + 100 | −100% (variety "DEA") |
| A2 + B2.3 | 150 + 150 | −100% (variety "HELIX") |

We claim:

1. A herbicidal composition comprising:
   (A) a herbicidally effective amount of a compound of the formula (I), a stereoisomer or an agriculturally useful salt thereof,

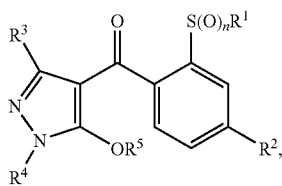

wherein $R^1$ represents a methyl group; $R^2$ represents a trifluoromethyl group; R3 represents a methyl group; $R^4$ represents a methyl group; $R^5$ represents hydrogen; and n is 2; and
   (B) an antidote-effective amount of at least one safener selected from the group consisting of mefenpyr-diethyl, isoxadifen-ethyl, cloquintocet-mexyl, and mixtures thereof.

2. The herbicidal composition according to claim 1, wherein the weight ratio herbicide:safener is from 1:100 to 100:1.

3. A method for controlling harmful plants in crops of useful plants, which comprises applying a herbicidally effective amount of a herbicidal composition according to claim 1, onto the harmful plants, plants, plant seeds or the area on which the plants grow.

4. A method for controlling harmful plants in crops of useful plants, which comprises applying a herbicidally effective amount of a herbicidal composition according to claim 2 onto the harmful plants, plants, plant seeds or the area on which the plants grow.

5. The method according to claim 3, wherein the plants originate from the group consisting of corn, wheat, rye, barley, oats, rice, sorghum, cotton, sugar cane and soya.

6. The method according to claim 4, wherein the plants originate from the group consisting of corn, wheat, rye, barley, oats, rice, sorghum, cotton, sugar cane and soya.

7. The method according to claim 3, wherein the plants are genetically modified.

8. The method according to claim 4, wherein the plants are genetically modified.

9. The method according to claim 5, wherein the plants are genetically modified.

10. The method according to claim 6, wherein the plants are genetically modified.

* * * * *

UNITED STATES PATENT AND TRADEMARK OFFICE
CERTIFICATE OF CORRECTION

PATENT NO. : 7,579,301 B2  Page 1 of 1
APPLICATION NO. : 11/069222
DATED : August 25, 2009
INVENTOR(S) : Monika Schmitt et al.

It is certified that error appears in the above-identified patent and that said Letters Patent is hereby corrected as shown below:

In Claim 1, Column 13, line 4, "stercoisomer" should be corrected to read --stereoisomer--.

In Claim 1, Column 13, line 6, "R3" should be corrected to read --$R^3$--.

Signed and Sealed this

Fifth Day of January, 2010

David J. Kappos
*Director of the United States Patent and Trademark Office*